(12) United States Patent
Shimoda et al.

(10) Patent No.: US 9,498,623 B2
(45) Date of Patent: Nov. 22, 2016

(54) REHABILITATION SYSTEM

(71) Applicant: TOYOTA JIDOSHA KABUSHIKI KAISHA, Toyota-shi, Aichi-ken (JP)

(72) Inventors: Shingo Shimoda, Kasugai (JP); Fady SK Shibata Alnajjar, Nagoya (JP); Vincent Berenz, Nagoya (JP); Hitoshi Yamada, Nagakute (JP); Masashi Yamashita, Miyoshi (JP); Takashi Izuo, Toyota (JP); Soya Takagi, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 10 days.

(21) Appl. No.: 14/613,788

(22) Filed: Feb. 4, 2015

(65) Prior Publication Data
US 2015/0217112 A1 Aug. 6, 2015

(30) Foreign Application Priority Data
Feb. 6, 2014 (JP) .................................. 2014-021530

(51) Int. Cl.
| | | |
|---|---|---|
| A61N 1/36 | (2006.01) |
| A61B 5/0488 | (2006.01) |
| A61B 5/11 | (2006.01) |
| A61B 5/00 | (2006.01) |
| A61H 1/02 | (2006.01) |

(52) U.S. Cl.
CPC ......... *A61N 1/36003* (2013.01); *A61B 5/0488* (2013.01); *A61B 5/1128* (2013.01); *A61B 5/7278* (2013.01); *A61B 5/742* (2013.01); *A61H 1/0274* (2013.01); *A61H 2201/10* (2013.01); *A61H 2201/1635* (2013.01); *A61H 2201/5043* (2013.01); *A61H 2201/5058* (2013.01); *A61H 2205/06* (2013.01); *A61H 2230/605* (2013.01)

(58) Field of Classification Search
None
See application file for complete search history.

(56) References Cited

U.S. PATENT DOCUMENTS

| 8,165,685 | B1 * | 4/2012 | Knutson | ............ A61N 1/36003 607/2 |
| 2008/0234781 | A1 * | 9/2008 | Einav | ................. A61N 1/36014 607/48 |
| 2012/0179075 | A1 * | 7/2012 | Perry | ..................... B25J 9/0006 601/33 |

FOREIGN PATENT DOCUMENTS

| JP | H08-229015 A | 9/1996 |
| JP | 2003-339908 A | 12/2003 |

* cited by examiner

*Primary Examiner* — Brian T Gedeon
*Assistant Examiner* — Ankit D Tejani
(74) *Attorney, Agent, or Firm* — Oliff PLC

(57) ABSTRACT

A rehabilitation system that assists an action of a paretic arm due to brain damage, such as a stroke, includes: a detecting unit configured to detect an assist action that a healthy arm assists the paretic arm; an assist unit configured to cause the paretic arm to carry out bending and stretching actions; an adjustment unit configured to adjust an operation timing, operation speed, bending load or stretching load of the assist unit in response to detection of the assist action by the detecting unit; and a control unit configured to cause the assist unit to operate in accordance with the operation timing, operation speed, bending load or stretching load, adjusted by the adjustment unit.

9 Claims, 5 Drawing Sheets

REHABILITATION SYSTEM

INCORPORATION BY REFERENCE

The disclosure of Japanese Patent Application No. 2014-021530 filed on Feb. 6, 2014 including the specification, drawings and abstract is incorporated herein by reference in its entirety.

BACKGROUND OF THE INVENTION

1. Field of the Invention

The invention relates to a rehabilitation system that assists an action of a paretic arm due to brain damage, such as a stroke.

2. Description of Related Art

A stroke patient mostly has a paretic arm or leg on one side. To move the paretic arm or leg, a brain and muscles need to operate normally. A process of generating myoelectricity by one's own intention is important for such a hemiplegia patient in rehabilitation. A system described in Japanese Patent Application Publication No. 8-229015 (JP 8-229015 A) includes myoelectric potential detecting means for detecting a myoelectricity that is generated as a result of human's muscle activity. The system displays information, detected by the myoelectric potential detecting means, on a display unit. Thus, the system causes a patient to recognize that the body is moved by the action of the patient by oneself. A system described in Japanese Patent Application Publication No. 2003-339908 (JP 2003-339908 A) includes myoelectric potential sensors in correspondence with muscles and displays indicators corresponding to the myoelectric potential sensors as a human icon. Thus, it is possible to acquire the state of the muscle of each portion.

SUMMARY OF THE INVENTION

An absolutely immovable paretic arm does not generate myoelectricity. Even when an absolutely immovable paretic arm is moved by external assistance, myoelectricity is not generated. However, the inventors found a matter that even a paretic arm that does not generate myoelectricity with external assistance generates myoelectricity if the paretic arm is supported by one's own healthy arm.

The invention provides a rehabilitation system that is able to improve rehabilitation effect by particularly causing a paretic arm, which does not generate myoelectricity, to generate myoelectricity.

An aspect of the invention relates to a rehabilitation system that assists an action of a paretic arm due to brain damage. The rehabilitation system includes: a detecting unit configured to detect an assist action that a healthy arm assists the paretic arm; an assist unit configured to cause the paretic arm to carry out bending and stretching actions; an adjustment unit configured to adjust an operation timing, operation speed, bending load or stretching load of the assist unit in response to detection of the assist action by the detecting unit; and a control unit configured to cause the assist unit to operate in accordance with the operation timing, operation speed, bending load or stretching load, adjusted by the adjustment unit.

In the above aspect, the detecting unit may be configured to detect support of a forearm of the paretic arm or a hand of the paretic arm by a hand of the healthy arm.

In the above aspect, the detecting unit may include a first wearing device and a second wearing device, the first wearing device may be worn on the hand of the healthy arm, the second wearing device may be worn on the forearm of the paretic arm or the hand of the paretic arm, and the detecting unit may be configured to detect the assist action through contact of the first wearing device with the second wearing device or pressing of the first wearing device against the second wearing device.

In the above aspect, the rehabilitation system may further include: a myoelectric sensor configured to detect a myoelectric potential of the paretic arm; and an output unit configured to inform that the myoelectric potential has been detected by the myoelectric sensor.

In the above aspect, the assist unit may be a myoelectric stimulation device. The myoelectric stimulation device may be configured to stimulate the paretic arm in accordance with the myoelectric potential detected by the myoelectric sensor or a muscle synergy calculated based on the myoelectric potential detected by the myoelectric sensor.

In the above aspect, the output unit may be configured to display a video image of movement of the paretic arm in response to detection of the myoelectric potential by the myoelectric sensor or a muscle synergy calculated based on the myoelectric potential detected by the myoelectric sensor.

In the above aspect, the output unit may be configured to display, through a head-worn display, the myoelectric potential detected by the myoelectric sensor or a muscle synergy calculated based on the myoelectric potential detected by the myoelectric sensor and a video image of movement of the paretic arm in a superimposed manner.

In the above aspect, the adjustment unit may be configured to adjust the operation timing, operation speed, bending load or stretching load of the assist unit in response to detection of the myoelectric potential by the myoelectric sensor or a muscle synergy calculated based on the myoelectric potential detected by the myoelectric sensor:

In the above aspect, the adjustment unit may be configured to adjust the operation timing, operation speed, bending load or stretching load of the assist unit by comparing a target value generated by inputting a myoelectric potential or muscle synergy of the healthy arm or an arm of a healthy person as a model with the myoelectric potential detected by the myoelectric sensor or a muscle synergy calculated based on the myoelectric potential detected by the myoelectric sensor.

According to the aspect of the invention, it is possible to improve rehabilitation effect by particularly causing a paretic arm, which does not generate myoelectricity, to generate myoelectricity.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

Figure 1:
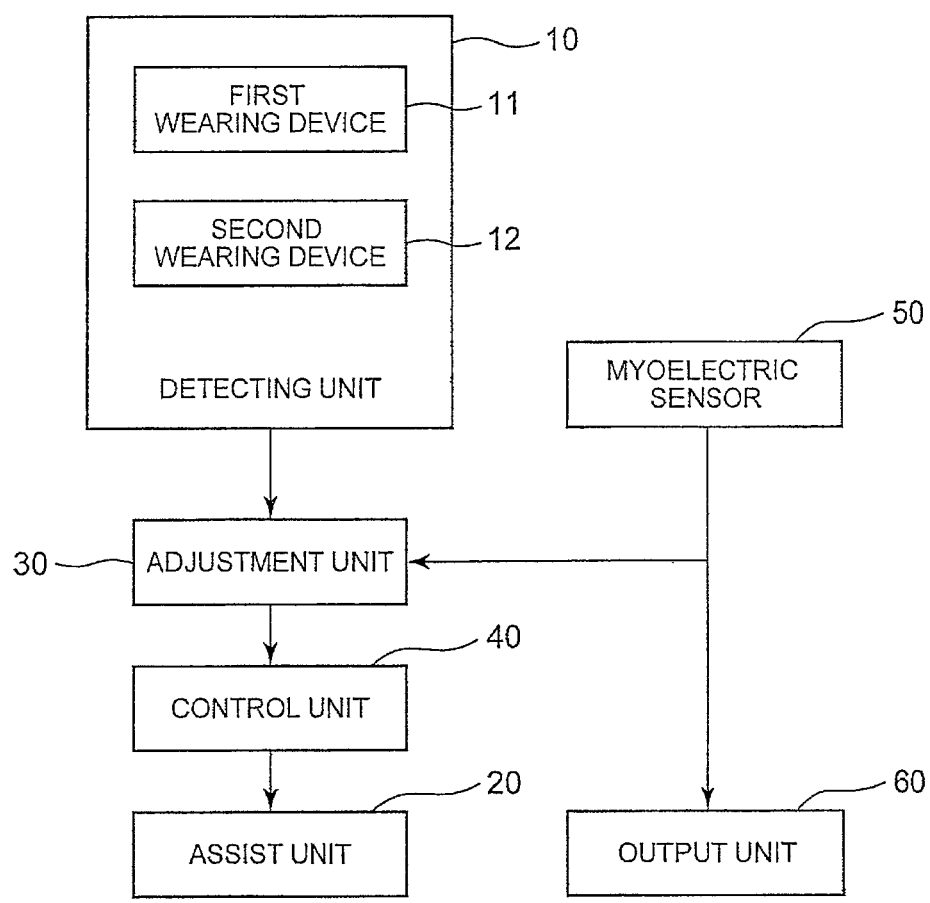
FIG. 1 is a block diagram for implementing a rehabilitation system according to an embodiment of the invention.

A first embodiment of the invention provides a rehabilitation system. The rehabilitation system includes a detecting unit, an assist unit, an adjustment unit and a control unit. The detecting unit detects an assist action that a healthy arm assists a paretic arm. The assist unit causes the paretic arm to carry out bending and stretching actions. The adjustment unit adjusts an operation timing, operation speed, bending load or stretching load of the assist unit in response to detection of the assist action by the detecting unit. The control unit causes the assist unit to operate in accordance with the operation timing, operation speed, bending load or stretching load, adjusted by the adjustment unit. According to the present embodiment, the operation timing, operation speed, bending load or stretching load is adjusted in response to the fact that the healthy arm assists the paretic arm as a trigger. Therefore, it is easy to generate myoelectricity caused by self-support, so it is possible to improve rehabilitation effect.

A second embodiment of the invention provides a rehabilitation system in which, in the rehabilitation system according to the first embodiment, the detecting unit detects support of a forearm of the paretic arm or a hand of the paretic arm by a hand of the healthy arm. According to the present embodiment, by memorizing a state where a body image is easily recalled, the effect of self-support improves.

A third embodiment of the invention provides a rehabilitation system in which, in the rehabilitation system according to the second embodiment, the detecting unit includes a first wearing device and a second wearing device. The first wearing device is worn on the hand of the healthy arm. The second wearing device is worn on the forearm of the paretic arm or the hand of the paretic arm. The detecting unit detects the assist action through contact of the first wearing device with the second wearing device or pressing of the first wearing device against the second wearing device. According to the present embodiment, it is possible to achieve reliable self-support.

A fourth aspect of the invention provides a rehabilitation system in which the rehabilitation system according to any one of the first to third embodiments further includes a myoelectric sensor and an output unit. The myoelectric sensor detects a myoelectric potential of the paretic arm. The output unit informs that the myoelectric potential has been detected by the myoelectric sensor. According to the present embodiment, it is possible to facilitate rehabilitation by informing detection of the myoelectric potential of the paretic arm.

A fifth embodiment of the invention provides a rehabilitation system in which, in the rehabilitation system according to the fourth embodiment, the assist unit is a myoelectric stimulation device. The myoelectric stimulation device stimulates the paretic arm in accordance with the myoelectric potential detected by the myoelectric sensor or a muscle synergy calculated on the basis of the myoelectric potential detected by myoelectric sensor. According to the present embodiment, it is possible to improve the control accuracy and response speed of the assist unit as compared to a mechanical assist unit.

A sixth embodiment of the invention provides a rehabilitation system in which, in the rehabilitation system according to the fourth or fifth embodiment, the output unit displays a video image of movement of the paretic arm in response to detection of the myoelectric potential by the myoelectric sensor or a muscle synergy calculated on the basis of the myoelectric potential detected by the myoelectric sensor. According to the present embodiment, it is possible to further facilitate rehabilitation owing to visual effect.

A seventh embodiment of the invention provides a rehabilitation system in which, in the rehabilitation system according to the fourth or fifth embodiment, the output unit displays, through a head-worn display, the myoelectric potential detected by the myoelectric sensor or a muscle synergy calculated on the basis of the myoelectric potential detected by the myoelectric sensor and a video image of movement of the paretic arm in a superimposed manner. According to the present embodiment, a patient is allowed to deeply concentrate into augmented reality, so it is possible to further facilitate rehabilitation owing to visual effect.

An eighth embodiment of the invention provides a rehabilitation system in which, in the rehabilitation system according to any one of the fourth to seventh embodiments, the adjustment unit adjusts the operation timing, operation speed, bending load or stretching load of the assist unit in response to detection of the myoelectric potential by the myoelectric sensor or a muscle synergy calculated on the basis of the myoelectric potential detected by the myoelectric sensor. According to the present embodiment, by adjusting the operation timing, operation speed, bending load or stretching load of the assist unit in response to detection of an actual myoelectric potential of the paretic arm, myoelectricity is easily generated, so it is possible to improve rehabilitation effect.

A ninth embodiment of the invention provides a rehabilitation system in which, in the rehabilitation system according to any one of the fourth to seventh embodiments, the adjustment unit adjusts the operation timing, operation speed, bending load or stretching load of the assist unit by comparing a target value generated by inputting a myoelectric potential or muscle synergy of the healthy arm or an arm of a healthy person as a model with the myoelectric potential detected by the myoelectric sensor or a muscle synergy calculated on the basis of the myoelectric potential detected by the myoelectric sensor. According to the present embodiment, it is possible to carry out assistance according to the degree of recovery.

Embodiment

FIG. 1 is a block diagram for implementing a rehabilitation system according to an embodiment of the invention. The rehabilitation system according to the embodiment of the invention is a rehabilitation system that assists an action of a paretic arm due to brain damage, such as a stroke. The rehabilitation system includes a detecting unit 10, an assist unit 20, an adjustment unit 30 and a control unit 40. The detecting unit 10 detects an assist action that a healthy arm assists the paretic arm. The assist unit 20 causes the paretic arm to carry out bending and stretching actions. The adjustment unit 30 adjusts an operation timing, operation speed, bending load or stretching load of the assist unit 20 in response to detection of the assist action by the detecting unit 10. The control unit 40 causes the assist unit 20 to operate in accordance with the operation timing, operation speed, bending load or stretching load, adjusted by the adjustment unit 30.

The detecting unit 10 detects support of a forearm of the paretic arm or a hand of the paretic arm by a hand of the healthy arm, that is, an assisting action (assist action). As shown in FIG. 1, the detecting unit 10 includes a first wearing device 11 and a second wearing device 12. The first wearing device 11 is worn on the hand of the healthy arm. The second wearing device 12 is worn on the forearm of the paretic arm or the hand of the paretic arm. The detecting unit 10 detects the assist action through contact of the first wearing device 11 with the second wearing device 12 or pressing of the first wearing device 11 against the second wearing device 12. For example, it is applicable that the first wearing device 11 is formed of a glove including a first electrode, the second wearing device 12 is formed of a glove including a second electrode, and the detecting unit 10 detects contact of the first electrode with the second electrode as movement of the healthy arm for assisting the paretic arm. Alternatively, it is applicable that the first wearing device 11 is formed of a glove including a first pressing switch, the second wearing device 12 is formed of a glove including a second pressing switch, and the detecting unit 10 detects pressing of the first pressing switch against the second pressing switch as movement of the healthy arm for assisting the paretic arm. The detecting unit 10 not only detects a change between an on state and an off state resulting from contact or pressing as the assist action but also may detect a pressing value. The detecting unit 10 may be formed of a motion capture. The assist unit 20 is an actuator that bends or stretches the forearm with respect to an upper arm.

The adjustment unit 30 starts the operation of the assist unit 20 when the detecting unit 10 detects the assist action of the healthy arm. By starting the operation of the assist unit 20, support by the healthy arm is assisted, and it is possible to make a patient to recall the body image. The adjustment unit 30 increases the operation speed of the assist unit 20 when the detecting unit 10 detects the assist action of the healthy arm. By increasing the operation speed of the assist unit 20, support by the healthy arm is assisted, and it is possible to make a patient to recall the body image. Conversely, the adjustment unit 30 may reduce the operation speed of the assist unit 20 when the detecting unit 10 detects the assist action of the healthy arm. By reducing the operation speed of the assist unit 20, support force by the healthy arm is increased, and it is possible to cause a patient to recall the body image. The adjustment unit 30 reduces the bending load or stretching load of the assist unit 20 when the detecting unit 10 detects the assist action of the healthy arm. By reducing the bending load or stretching load of the assist unit 20, support by the healthy arm is assisted, and it is possible to cause a patient to recall the body image. Conversely, the adjustment unit 30 may increase the bending load or stretching load of the assist unit 20 when the detecting unit 10 detects the assist action of the healthy arm. By increasing the bending load or stretching load of the assist unit 20, support force by the healthy arm is increased, and it is possible to cause a patient to recall the body image. In this way, the adjustment unit 30 adjusts at least any one of the operation timing, operation speed, bending load or stretching load of the assist unit 20, and may adjust any two or more of the operation timing, operation speed, bending load and stretching load of the assist unit 20 in combination.

When the detecting unit 10 detects the pressing value, it is possible to change the operation timing, operation speed, bending load or stretching load of the assist unit 20 in accordance with the magnitude of the pressing value. In this way, the rehabilitation system according to the present embodiment adjusts the operation timing, operation speed, bending load or stretching load in response to the fact that the healthy arm assists the paretic arm as a trigger. Thus, it is easy to generate myoelectricity caused by self-support, so it is possible to improve rehabilitation effect.

The rehabilitation system according to the present embodiment further includes a myoelectric sensor 50 and an output unit 60. The myoelectric sensor 50 detects the myoelectric potential of a biceps muscle of arm, triceps muscle of arm, or the like, of the paretic arm. The output unit 60 informs that the myoelectric potential has been detected by the myoelectric sensor 50. By informing detection of the myoelectric potential of the paretic arm, it is possible to facilitate rehabilitation. For example, the following sensor may be used as the myoelectric sensor 50. A plurality of electrodes are mounted on a muscle to be measured, a reference electrode band and a power supply are connected to the plurality of electrodes, and the waveform of the amount of activity of the muscle is measured. For example, display means is used as the output unit 60. The output unit 60 displays a video image of movement of the paretic arm in response to detection of the myoelectric potential by the myoelectric sensor 50. By displaying the video image of movement of the paretic arm with the display means, it is possible to further facilitate rehabilitation owing to visual effect. The video image of movement of the paretic arm may be created by capturing the action of the healthy arm and then inverting the action data of the healthy arm or may be created by, computer graphic. Alternatively, on the display means, the size of a display object may be changed in accordance with the magnitude of a myoelectricity value. The output unit 60 may output sound in addition to a display. The adjustment unit 30 is able to adjust the operation timing, operation speed, bending load or stretching load of the assist unit 20 in response to detection of the myoelectric potential by the myoelectric sensor 50. By adjusting the operation timing, operation speed, bending load or stretching load of the assist unit 20 in response to detection of an actual myoelectric potential of the paretic arm, it is easy to generate myoelectricity, and it is possible to improve rehabilitation effect.

The adjustment unit 30 starts the operation of the assist unit 20 when the myoelectric sensor 50 detects the myoelectric potential. By starting the operation of the assist unit 20, it is possible to recognize generation of an actual myoelectric potential, so it is possible to improve rehabilitation effect. The adjustment unit 30 increases the operation speed of the assist unit 20 when the myoelectric sensor 50 detects the myoelectric potential. By increasing the operation speed of the assist unit 20, it is possible to recognize generation of an actual myoelectric potential, so it is possible to improve rehabilitation effect. Conversely, the adjustment unit 30 may reduce the operation speed of the assist unit 20 when the myoelectric sensor 50 detects the myoelectric potential. By reducing the operation speed of the assist unit 20, it is possible to recognize generation of an actual myoelectric potential, so it is possible to improve rehabilitation effect. The adjustment unit 30 reduces the bending load or stretching load of the assist unit 20 when the myoelectric sensor 50 detects the myoelectric potential. By reducing the bending load or stretching load of the assist unit 20, it is possible to recognize generation of an actual myoelectric potential, so it is possible to improve rehabilitation effect. Conversely, the adjustment unit 30 may increase the bending load or stretching load of the assist unit 20 when the myoelectric sensor 50 detects the myoelectric potential. By increasing the bending load or stretching load of the assist unit 20, it is possible to recognize generation of an actual myoelectric potential, so it is possible to improve rehabilitation effect.

Adjustment by the adjustment unit 30, which is carried out in response to detection of the myoelectric potential by the myoelectric sensor 50, is carried out together with adjustment of the assist action that is detected by the detecting unit 10. The adjustment unit 30 is able to start the operation of the assist unit 20 in response to both detection of the assist action by the detecting unit 10 and detection of the myoelectric potential by the myoelectric sensor 50. Alternatively, the adjustment unit 30 may start the operation of the assist unit 20 in response to one of detection of the assist action by the detecting unit 10 and detection of the myoelectric potential by the myoelectric sensor 50. Alternatively, the adjustment unit 30 may start the operation of the assist unit 20 in response to detection of the assist action by the detecting unit 10, and may adjust the operation speed, bending load or stretching load of the assist unit 20 in response to detection of the myoelectric potential by the myoelectric sensor 50. Alternatively, the adjustment unit 30 may increase the operation speed of the assist unit 20 or reduce the operation speed of the assist unit 20 in response to both detection of the assist action by the detecting unit 10 and detection of the myoelectric potential by the myoelectric sensor 50. Alternatively, the adjustment unit 30 may increase the operation speed of the assist unit 20 or reduce the operation speed of the assist unit 20 in response to one of detection of the assist action by the detecting unit 10 and detection of the myoelectric potential by the myoelectric sensor 50. Alternatively, the adjustment unit 30 may increase the operation speed of the assist unit 20 or reduce the operation speed of the assist unit 20 in response to detection of the assist action by the detecting unit 10, and may adjust the bending load or stretching load in response to detection of the myoelectric potential by the myoelectric sensor 50. The adjustment unit 30 reduces the bending load or stretching load of the assist unit 20 or increases the bending load or stretching load of the assist unit 20 in response to both detection of the assist action by the detecting unit 10 and detection of the myoelectric potential by the myoelectric sensor 50. Alternatively, the adjustment unit 30 may reduce the bending load or stretching load of the assist unit 20 or increase the bending load or stretching load of the assist unit 20 in response to one of detection of the assist action by the detecting unit 10 and detection of the myoelectric potential by the myoelectric sensor 50. Alternatively, the adjustment unit 30 may reduce the bending load or stretching load of the assist unit 20 or increase the bending load or stretching load of the assist unit 20 in response to detection of the assist action by the detecting unit 10, and may adjust the operation speed of the assist unit 20 in response to detection of the myoelectric potential by the myoelectric sensor 50.

Adjustment by the adjustment unit 30, which is carried out in response to detection of the myoelectric potential by the myoelectric sensor 50, may be carried out instead of adjustment of the assist action that is detected by the detecting unit 10. The adjustment unit 30 may adjust the operation timing, operation speed, bending load or stretching load of the assist unit 20 by comparing a target value generated by inputting the myoelectric potential of the healthy arm as a model with the myoelectric potential detected by the myoelectric sensor 50. As a result, it is possible to perform assistance with the use of the assist unit 20 according to the degree of recovery. The target value may be generated by inputting the myoelectric potential of a healthy person in an ideal state as a model, instead of the myoelectric potential of the healthy arm.

Figure 2:
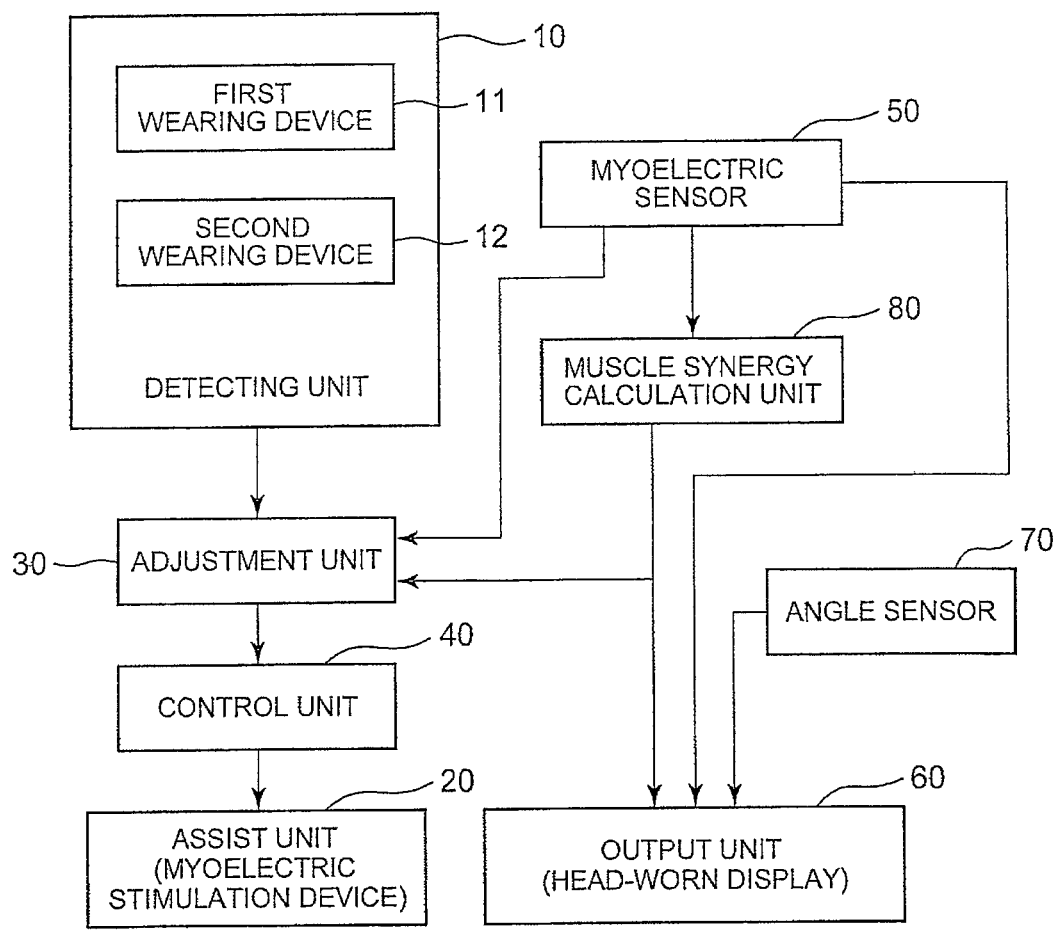
FIG. 2 is a block diagram for implementing a rehabilitation system according to another embodiment of the invention.

FIG. 2 is a block diagram for implementing a rehabilitation system according to another embodiment of the invention. Only the components different from those of the above-described embodiment will be described. Like reference numerals denote the same functional units, and the description thereof is omitted. In the present embodiment, the assist unit 20 uses a myoelectric stimulation device instead of the actuator. The rehabilitation system further includes a muscle synergy calculation unit 80. The muscle synergy calculation unit 80 calculates a muscle synergy on the basis of the myoelectric potential detected by the myoelectric sensor 50. The myoelectric stimulation device applies electrical stimulation in accordance with the calculated result of the muscle synergy calculation unit 80, and causes the forearm to bend or stretch with respect to the upper arm. The muscle synergy is a form of expression of a phenomenon that, when a human performs a behavior or performs a task consisting of one or more behaviors, a plurality of muscles cooperatively work with redundancy. In the present embodiment, the adjustment unit 30 is able to adjust the operation timing, operation speed, bending load or stretching load of the assist unit 20 in response to the muscle synergy calculated on the basis of the myoelectric potential detected by the myoelectric sensor 50. The adjustment unit 30 adjusts the operation timing, operation speed, bending load or stretching load of the assist unit 20 by comparing a target value generated by inputting a muscle synergy of the healthy arm as a model with a muscle synergy calculated on the basis of the myoelectric potential detected by the myoelectric sensor 50. Thus, it is possible to perform assistance according to the degree of recovery with the use of the assist unit 20. The target value may be generated by inputting a muscle synergy of a healthy person in an ideal state as a model, instead of the muscle synergy of the healthy arm. In the present embodiment, the output unit 60 displays, through a head-worn display, the myoelectric potential detected by the myoelectric sensor 50 or the muscle synergy based on the myoelectric potential detected by the myoelectric sensor 50 and a video image of movement of the paretic arm in a superimposed manner. For example, a head mount display may be used as the head-worn display. The head-worn display includes an angle sensor 70. The angle sensor 70 detects the angle of a head. The output unit 60 displays a video image (augmented reality) according to the head angle detected by the angle sensor 70 on the head-worn display. In this way, a patient wears the head-worn display; and an arm created by computer graphic in accordance with the myoelectric potential or the muscle synergy and the actual arm of the patient are displayed in a superimposed manner. Thus, the patient is allowed to concentrate into augmented reality, so rehabilitation effect improves. The magnitude of the muscle synergy may be converted to the color image of a skin and then projected onto the atm of the patient. When augmented reality is displayed, the assist unit 20 is not displayed and a video image is displayed as if only the arm of the patient is moving by itself. Thus, the patient is allowed to concentrate into augmented reality, so rehabilitation effect further improves.

Calculation of the muscle synergy will be described in more detail. Initially, the myoelectric sensor 50 acquires time-series myoelectric potentials of each of muscles 1, 2, . . . , m while a patient is performing a behavior. In the present embodiment, myoelectric potentials at m points of a body of the patient are measured. Points at which a myoelectric potential should be measured are muscles associated with the behavior (for example, bending and stretching of right hand) of a portion (for example, right hand) for training.

Measurement is performed from the start of a behavior to the end of the behavior at constant time intervals. A value of myoelectric potential of the i-th muscle at the j-th timing is stored in the i-th row and j-th column element M[i,j] of a myoelectric potential matrix M. That is, the myoelectric potential matrix M is configured such that a row vector $M^{(1)}$ consisting of time-series myoelectric potentials of the muscle 1, a row vector $M^{(2)}$ consisting of time-series myoelectric potentials of the muscle 2, . . . , and a row vector $M^{(m)}$ consisting of time-series myoelectric potentials of the muscle in are arranged in rows.

Thus, the number of rows of the myoelectric potential matrix M is m. The number of columns of the myoelectric potential matrix M changes with the time length of measurement, that is, the time length of a behavior, and the frequency or interval of measurement during the behavior.

In this way, when the myoelectric potential matrix M is acquired, the muscle synergy calculation unit 80 calculates a muscle synergy matrix W, a control matrix C and an error matrix E so that M=WC+E. At this time, non-negative matrix factorization is used.

Hereinafter, for the sake of easy understanding, description will be made by omitting a suffix$_k$ where appropriate.

In non-negative matrix factorization, the degree of error is minimized or a similarity L is maximized.

Where the number of columns of the myoelectric potential matrix M, the number of columns of the control matrix C and the number of columns of the error matrix E all are t, the number of rows of the myoelectric potential matrix M, the number of rows of the muscle synergy matrix W and the number of rows of the error matrix E all are m, and the number of columns of the muscle synergy matrix W and the number of rows of the control matrix C all are n, the similarity L may be defined as follows.

$$L=1-1/m \times \Sigma_{i=1}^{m} \sqrt{[\Sigma_{j=1}^{1} E[i,j]^2]}/\sqrt{[\Sigma_{j=1}^{1} (WC)[i,j]^2]}$$

Here, n is a numeric value that indicates the number of synergies. Generally, when n is increased, L also increases. An appropriate value of n may also be determined as follows by using non-negative matrix factorization as needed.

Generally, in non-negative matrix factorization, it is desired to select the number of synergies n so that the similarity L is higher than or equal to 70%. On the other hand, when the number of synergies n is too large, not only a calculation load increases but also over-adaptation occurs, with the result that an appropriate process is not executed on the contrary.

Therefore, the following method is used.

That is, for each of n=1, 2, 3, 4, . . . , the above-described similarity L is calculated.

Figure 3:
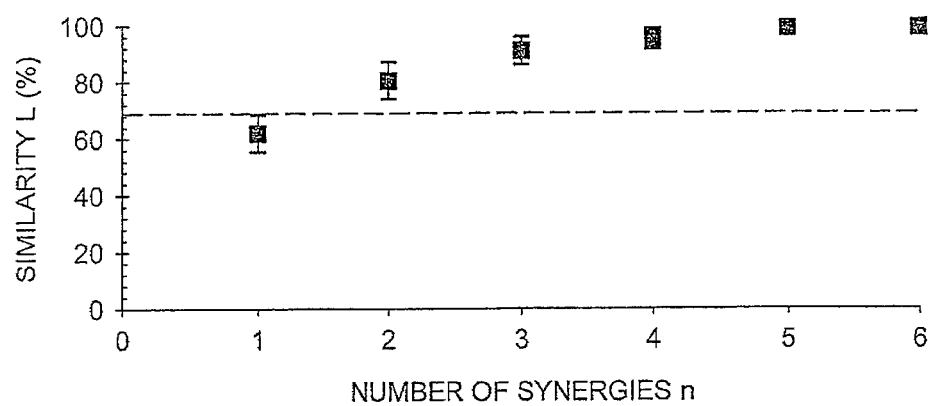
FIG. 3 is a graph that shows a similarity L calculated for the number of synergies n for a behavior.

FIG. 3 is a graph that shows the similarity L calculated for the number of synergies n for a behavior. Hereinafter, description will be made with reference to FIG. 3.

In FIG. 3, the abscissa axis Number of synergies n represents the number of synergies n, and the ordinate axis Similarity L (%) represents the similarity L. As shown in FIG. 3, it appears that, as the number of synergies n increases, the similarity L also increases; however, the degree of increase in similarity L is saturated at the number of synergies n of about 5, and the similarity L is higher than or equal to 70%. Thus, a numeric value before or after the beginning of saturation, for example, 4, 5 or 6, may be employed as the number of synergies n for the following calculation.

The number of synergies n may be a value different for each individual patient. Alternatively, the number of synergies n may be a value common to all the patients because it is presumable that there is no large difference in the number of synergies when a human performs a behavior. In the latter case, some patients are caused to perform a behavior experimentally in advance, an adequate value of n is determined by non-negative matrix factorization, and, thereafter, the determined value of n is directly used for the other patients as well.

In this model, it is assumed that, when the central nerve of a patient supplies n control signals $C^{(1)}, C^{(2)}, \ldots, C^{(n)}$ to m muscles, the muscle 1 attempts to move so that the myoelectric potential $WC^{(1)}$ is satisfied, the muscle 2 attempts to move so that the myoelectric potential $WC^{(2)}$ is satisfied, . . . , and the muscle m attempts to move so that the myoelectric potential $WC^{(m)}$ is satisfied.

Figure 4A:
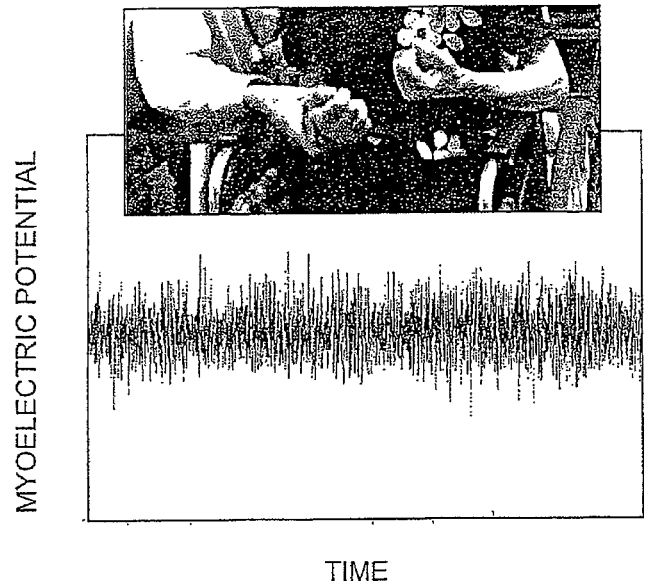
FIG. 4A and FIG. 4B are characteristic graphs that respectively show experimental examples.
Figure 4B:
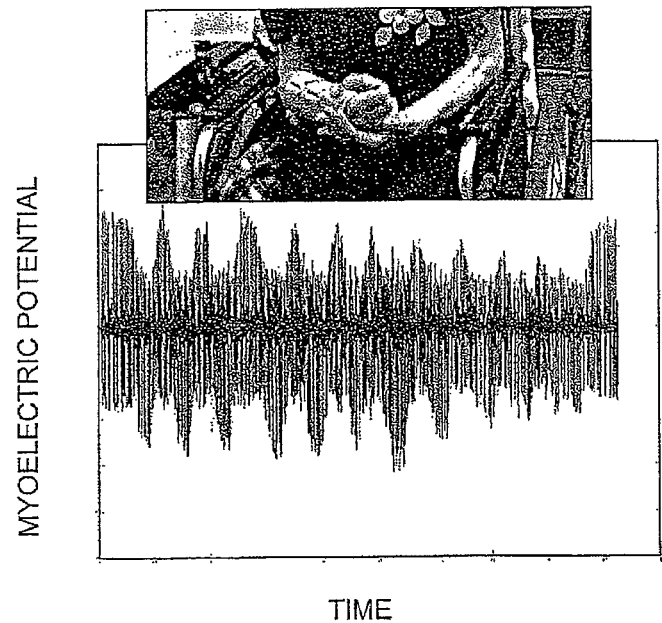
Figure 5:
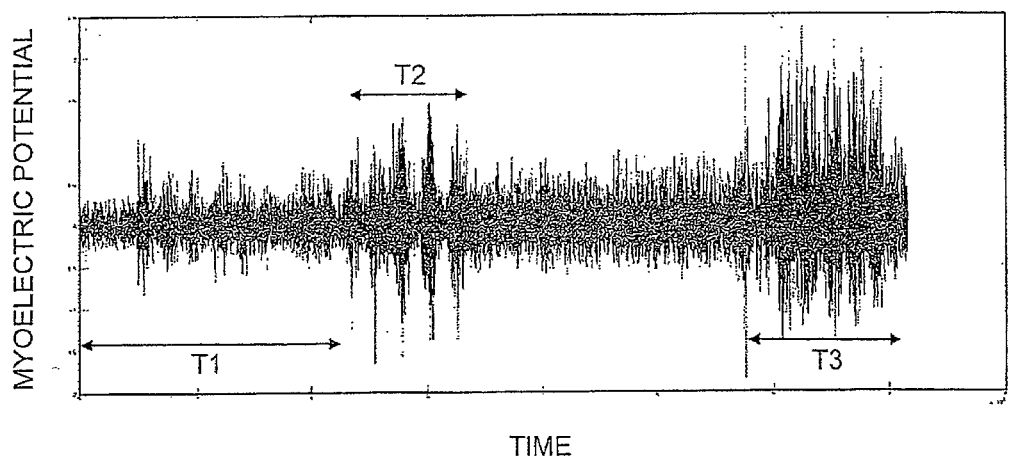
FIG. 5 is a characteristic graph that shows an experimental example.

FIG. 4A to FIG. 5 are characteristic graphs that respectively show experimental examples. In these experiments, a hemiplegia patient of which a right arm is an absolutely immovable paretic arm is employed as a subject. FIG. 4A is a characteristic graph of the myoelectric potential at the time when the paretic arm is moved with external assistance. FIG. 4B is a characteristic graph of the myoelectric potential at the time when the paretic arm is moved by self-support, that is, the healthy arm. It appears that no myoelectricity is generated in FIG. 4A and myoelectricity is apparently generated in FIG. 4B.

FIG. 5 is a characteristic graph of the myoelectric potential of the same subject who has undergone rehabilitation through self-support for about two months. In FIG. 5, a time during which the paretic arm is intended to be moved without support is denoted by T1, a time during which the paretic arm is moved with external assistance is denoted by T2, and a time during which the paretic arm is moved with the healthy arm through self-support is denoted by T3. No myoelectricity is generated during the time T1; whereas myoelectricity is generated during the time T2. In this way, when the patient undergoes rehabilitation through self-support, myoelectricity is generated even with external assistance. When the paretic arm is moved with the healthy arm through self-support as shown during the time T3, it appears that a larger myoelectricity than that in the case of external assistance is generated.

According to the invention, it is possible to generate myoelectricity in the absolutely immovable paretic arm.

What is claimed is:

1. A rehabilitation system that assists an action of a paretic arm due to brain damage, the rehabilitation system comprising:
    a detecting unit configured to detect an assist action as that of a paretic arm as it is being assisted by a healthy arm;
    an assist unit configured to cause the paretic arm to carry out bending and stretching actions;
    an adjustment unit configured to adjust an operation timing, operation speed, bending load or stretching load of the assist unit in response to detection of the assist action by the detecting unit; and
    a control unit configured to cause the assist unit to operate in accordance with the operation timing, operation speed, bending load or stretching load, adjusted by the adjustment unit.

2. The rehabilitation system according to claim 1, wherein the detecting unit is configured to detect support of a forearm of the paretic arm or a hand of the paretic arm by a hand of the healthy arm.

3. The rehabilitation system according to claim 2, wherein the detecting unit includes a first wearing device and a second wearing device, the first wearing device is worn on the hand of the healthy arm, the second wearing device is worn on the forearm of the paretic arm or the hand of the paretic arm, and the detecting unit is configured to detect the assist action through contact of the first wearing device with the second wearing device or pressing of the first wearing device against the second wearing device.

4. The rehabilitation system according to claim 1, further comprising:
   a myoelectric sensor configured to detect a myoelectric potential of the paretic arm; and
   an output unit configured to inform that the myoelectric potential has been detected by the myoelectric sensor.

5. The rehabilitation system according to claim 4, wherein the assist unit is a myoelectric stimulation device, and
   the myoelectric stimulation device is configured to stimulate the paretic arm in accordance with the myoelectric potential detected by the myoelectric sensor or a muscle synergy calculated based on the myoelectric potential detected by the myoelectric sensor.

6. The rehabilitation system according to claim 4, wherein the output unit is configured to display a video image of movement of the paretic arm in response to detection of the myoelectric potential by the myoelectric sensor or a muscle synergy calculated based on the myoelectric potential detected by the myoelectric sensor.

7. The rehabilitation system according to claim 4, wherein the output unit is configured to display, through a head-worn display, the myoelectric potential detected by the myoelectric sensor or a muscle synergy calculated based on the myoelectric potential detected by the myoelectric sensor and a video image of movement of the paretic arm in a superimposed manner.

8. The rehabilitation system according to claim 4, wherein the adjustment unit is configured to adjust the operation timing, operation speed, bending load or stretching load of the assist unit in response to detection of the myoelectric potential by the myoelectric sensor or a muscle synergy calculated based on the myoelectric potential detected by the myoelectric sensor.

9. The rehabilitation system according to claim 4, wherein the adjustment unit is configured to adjust the operation timing, operation speed, bending load or stretching load of the assist unit by comparing a target value generated by inputting a myoelectric potential or muscle synergy of the healthy arm or an arm of a healthy person as a model with the myoelectric potential detected by the myoelectric sensor or a muscle synergy calculated based on the myoelectric potential detected by the myoelectric sensor.

* * * * *